United States Patent [19]

Mann

[11] Patent Number: 5,673,586
[45] Date of Patent: Oct. 7, 1997

[54] ADHESION AND COHESION TESTING SYSTEM

[76] Inventor: George E. Mann, 1816 Oak St., Pasadena, Calif. 91030

[21] Appl. No.: 746,496

[22] Filed: Nov. 12, 1996

Related U.S. Application Data

[63] Continuation-in-part of Ser. No. 184,429, Jan. 29, 1994, Pat. No. 5,575,868, which is a continuation of Ser. No. 910,625, Jul. 8, 1992, abandoned.

[51] Int. Cl.$^6$ ............................................. G01N 19/08
[52] U.S. Cl. ................................. 73/150 A; 73/827
[58] Field of Search ....................... 73/150 R, 150 A, 73/827, 834, 835, 837, 838, 840; 156/64, 378; 118/712

[56] References Cited

U.S. PATENT DOCUMENTS

| | | | |
|---|---|---|---|
| 4,393,699 | 7/1983 | Seiler, Jr. | 73/150 A |
| 4,491,014 | 1/1985 | Seiler, Jr. | 73/150 A |

OTHER PUBLICATIONS

Optimization of Processing Variables Which Affect Adhesion of Organic Materials, A.B. Featherston, Vought CorporationDocument AD-A048467, Apr. 1977.
Measurement of Adhesion by a Blister Method, Hans Dannenberg J. of Applied Polymer Science, vol. V, No. 14, pp. 125–134 (1961).
The Continuum Interpretation for Fracture and Adhesion, M.L. Williams College of Engineering, University of Utah, J. of Applied Polymer Science, vol. 13 pp. 29–40 (1969).

*Primary Examiner*—Robert Raevis
*Attorney, Agent, or Firm*—Charles H. Thomas

[57] ABSTRACT

A method and system are provided for testing the adhesive strength of a bond between an adhesive, a coating such as paint, or some other material, and an underlying substrate to which the test substance is bonded. The test may be performed at room temperature or in an environmental chamber at extreme conditions. An aperture is formed through the substrate and a thin film is employed to cover the aperture. The film extends beyond the perimeter of the aperture in contact with a first surface of the substrate. A coating of adhesive, paint, adhesive tape, or any other substance to be tested is then applied atop the film and the surrounding surface of the substrate in a smooth, continuous layer. A membrane which maintains its elastic property with only minor yielding during the test is bonded to the test substance, either directly or by means of a layer of high-strength adhesive interposed therebetween. The adhesive strength of the bond between the membrane and the substance being tested must be greater than the bond between the substance being tested and the substrate. The test assembly thereby produced is clamped within a test fixture and pressure is applied through an aperture in the test fixture from the side of the substrate opposite the surface of the substrate to which the test substance is bonded. With increasing pressure the test substance and membrane are deformed at the aperture through the substrate until the critical pressure is reached and the bond between the test substance and the substrate fails.

20 Claims, 5 Drawing Sheets

ADHESION AND COHESION TESTING SYSTEM

BACKGROUND OF THE INVENTION

The present invention is a continuation-in-part of U.S. application Ser. No. 08/184,429 filed Jan. 29, 1994, now U.S. Pat. No. 5,575,868, which is an continuation of U.S. application Ser. No. 07/910,625, filed Jul. 8, 1992, abandoned.

This invention was made with government support under grant ECD 9119322 awarded by the National Science Foundation.

FIELD OF THE INVENTION

The present invention relates to a testing apparatus and a method for testing the bonding strengths and/or cohesion strengths of coatings and adhesives.

DESCRIPTION OF THE PRIOR ART

For many years those skilled in the art have attempted to find a suitable method for measuring adhesive strength which would provide results independent of the testing process. One such approach is a so-called "blister" method. In this process a fluid, either gas or liquid, is injected under the coating through a hole in its substrate forcing the coating to lift from the substrate in the form of a blister.

A promising enhancement of the blister technique was described by Dannenberg in 1960 (H. Dannenberg, "Measurement of Adhesion by a Blister Method", J. of Applied Polymer Science, Vol. V, No. 14, pp 125–134 (1961)). However, this process is complex and has not been widely accepted.

In 1977 A. B. Featherston described a further procedure involving the blister method for the evaluation of the adhesive strength of coatings (Optimization of Processing Variables Which Affect Adhesion of Organic Materials, reported in Vought Corporation Document AD-A048467, April 1977). None of the known blister testing methods has been widely accepted.

One of the principal problems associated with the use of the blister method to evaluate the adhesion of a coating is that the film of the coating will often rupture before the coating debonds from the substrate. Also, the varying elasticities of most coatings will cause varying relationships between the height and the diameter of the paint blister formed, thus producing varying test results. Additionally, to determine bonding strength the blister method requires measuring both the elevation of the paint or other coating from the underlying surface to which it is bonded as well as the pressure at which debonding occurs. This results in a complex calculation for materials with a nonlinear stress-strain relationship.

Another limitation common with conventional blister testing methods is that they must be conducted in a laboratory at normal room temperatures and are not suitable for testing at extreme environmental conditions, such as high or low temperatures.

My prior U.S. patent application Ser. No. 08/184,429 filed Jan. 29, 1994 describes certain devices and techniques which solve significant problems previously encountered in ascertaining the bonding strength of coatings and adhesives to underlying substrates. The entirety of the disclosure of my prior U.S. application Ser. No. 08/184,429 is incorporated herein by reference.

In addition to the advantages over the prior art provided by the invention of my prior U.S. application Ser. No. 08/184,429, the present invention has certain additional advantages. Specifically, in constructing a test device it is advisable to employ a substrate, which takes the form of a rigid structure typically formed of a hard material to which the coating or adhesive to be tested is often applied. Such substrates may take the form of sheets or plates of aluminum, stainless steel, plastics, wood and other rigid materials. In preparing a test device to measure the adhesive strength of a test substance such as an adhesive substance or a coating, such as paint, it is necessary to introduce a fluid under pressure between the test substance and the substrate so that the fluid exerts a force tending to separate the adhesive coating from the substrate.

A fluid passageway to an interface between the test substance and the substrate is most conveniently provided by forming an aperture in the substrate, typically by drilling. Once the fluid access aperture has been formed in the substrate, the adhesive or coating is applied across the expanse of the substrate. However, to obtain consistency of results it is important to avoid clogging the passageway with excess adhesive or coating, and also to avoid any irregularities in the demarcation between the adhesive or coating and the substrate where the adhesive or coating surrounds the aperture through the substrate. For example, where the substrate is formed of wood, slight splintering can occur around the edges when the aperture is drilled through the substrate. If the adhesive or coating is applied to the substrate up to the very edge of the fluid aperture, inconsistent results may occur due to irregularities at the circumference of the aperture on the face of the substrate to which the adhesive or coating is applied.

To avoid possible errors in measurement that might otherwise result, the present invention provides a system for eliminating the interface between the adhesive or coating at the fluid aperture while still maintaining a consistent, reproducible area within the perimeter of the substrate at which the adhesive or coating is bonded to the substrate.

In the prior system of my U.S. application Ser. No. 08/184,429 a consistent, reproducible peripheral area of bonding was provided by creating a consistent, reproducible area of absence of bonding between the test substance, namely the adhesive or coating, and the substrate, at the center of the test device. This central unbonded area was provided by the area of the fluid opening in the substrate. According to the present invention, however, this reproducible, consistent area of an absence of bonding between the test substance and the substrate is provided by forming the fluid aperture with a very small diameter, and by covering the fluid aperture with a patch formed of a thin film of known geometric dimensions. The film is positioned atop the substrate and extends beyond the edges of the aperture a sufficient distance to prevent the occurrence of any inconsistent test results that might otherwise occur if the adhesive or coating is applied to the substrate right up to the edges of the pressure aperture. Preferably, the thin film extends beyond the edges of the aperture at least about 0.125 inches throughout the perimeter of the aperture. Preferably also, the aperture has a circular cross section and the thin film is formed as a circular patch having a diameter at least twice that of the fluid aperture and positioned atop the substrate in coaxial alignment with the fluid aperture.

The use of a thin film cover that extends beyond the perimeter of the aperture has other advantages as well. By utilizing such a cover the need for a temporary plug in the fluid aperture is eliminated. That is, in my prior system a plug was temporarily inserted into the fluid aperture during the time that the adhesive or coating to be tested was applied to the upper surface of the substrate. The plug prevented the adhesive or coating from dripping down into the fluid aperture. By employing a thin film patch according to the present invention, however, no such plug is necessary.

The present invention has other advantages as well. Specifically, the apparatus and method employed allow testing of both cohesive and adhesive failure of a bond between a test substance and a substrate. In testing the strength of a bond for adhesive failure, the specimen is examined following testing to determine whether or not separation of the test substance has occurred at the interface between the test substance, namely between the adhesive substance or the coating, and the substrate. If the separation is at the interface between the test substance and the substrate, the critical pressure measured is indicative of the strength of the adhesive bond between the test substance and the substrate. This critical pressure for any particular test substance will vary, depending upon the substrate to which it bonds, since test substances will adhere with greater or lesser tenacity to substrates formed of different materials, or to substrates prepared differently prior to bonding.

On the other hand, failure may occur within the test substance itself. Internal cohesive failure occurs when the layer separates laterally within itself in a plane substantially normal to the direction in which the force of separation is applied. That is, in cohesive failure a portion of the test substance, namely the adhesive, coating, or tape being tested, remains attached to the substrate, while another portion of the test substance remains attached to the membrane. Separation therefore occurs within the test substance itself, and not at the interface between the test substance and either the substrate or the membrane. In this case the critical pressure creating the failure is indicative of the cohesive strength of the test substance.

Cohesive strength is evaluated within the test substance as the specific work of cohesive failure of the test substance. When cohesive failure occurs internally within the test substance, the substrate employed is not material to the test results as long as the adhesive strength of the bond between the test substance and the substrate exceeds the internal cohesive strength of internal bonding within the substance being tested.

SUMMARY OF THE INVENTION

The present invention provides a relatively simple adhesive strength testing method and system which provide consistent measurements of bonding strength, which does not require measuring the elevation of the test substance before separation, and which can be conducted in extreme environmental conditions.

The present invention uses increasing pressure against a membrane bonded to a coating to facilitate the determination of the adhesive bond strength between a coating and a substrate to which it is bonded by measuring the pressure required to debond the coating from the substrate. The present invention also facilitates the determination of the internal cohesive strength in the adhesive or coating itself. The adhesive and cohesive strengths may be determined at room temperatures or at extreme temperatures within an environmental chamber.

In one broad aspect the present invention may be considered to be a system for testing the strength of the bond between a test substance and a rigid substrate through which an aperture is defined. The system is comprised of a membrane with a first side bonded to the test substance, the adhesive strength of the bond between the membrane and the test substance being greater than the strength of the bond between the test substance and the substrate; a thin film for covering the aperture interposed between the test substance and the substrate atop the aperture and extending beyond the perimeter of the aperture; means for applying increasing pressure though the aperture in the substrate to debond the test substance from the substrate; and means for determining the critical pressure required to substantially debond a continuous periphery of an area in the test substance from the substrate, the critical pressure being directly related to the specific work of debonding.

Preferably, the means for determining the critical pressure further comprises means for determining the adhesive strength of the bond between the test substance and the substrate directly from the pressure required to cause substantial bond failure as a function of the specific work of debonding the test substance from the substrate.

In another broad aspect the present invention may be considered to be a system for testing the cohesive strength of a test substance bonded to a rigid substrate through which an aperture is defined. The system is comprised of a membrane with a first side bonded to the test substance, the adhesive strength of the bond between the membrane and the test substance being greater than the cohesive strength of the test substance; a thin film for covering the aperture interposed between the test substance and the substrate atop the aperture and extending beyond the perimeter of the aperture; means for applying increasing pressure through the aperture in the substrate to cause cohesive failure in the test substance; and means for determining the critical pressure required to cause cohesive failure around a continuous periphery of an area in the test substance, the critical pressure being directly related to the specific work of cohesive failure.

The failure of the test substance may occur as either a failure of the adhesive bond between the test substance and the substrate, or as an internal cohesive failure within the substance being tested itself. In either event the adhesive or cohesive strength is expressed as the specific work of debonding or cohesive failure, and is calculated using the critical pressure and a formula based upon constants inherent to the system. In some embodiments of the invention substrate reinforcements may be utilized and firmly secured to the substrate to prevent errors that might otherwise occur due to deflections in the substrate.

The system of the invention can be used to determine the strength of both adhesive and cohesive bonds holding the test substance to the substrate. When utilized to determine the adhesive strength of the bond between the test substance and the substrate at the interface therebetween, the means for determining the critical pressure is further comprised of means for measuring the pressure at the moment the bond between the test substance and the substrate fails. When the system is utilized to determine the cohesive strength of the test substance, the means for determining the critical pressure is comprised of means for determining the internal cohesive strength of the test substance directly from the pressure required to cause substantial cohesive failure therewithin as a function of the specific work of cohesive failure of the test substance. In this application the means for determining critical pressure further comprises means for measuring the pressure at the moment substantial cohesive failure within the test substance occurs.

In preferred embodiments of the invention the membrane employed remains approximately elastic when subjected to the pressure applied to debond the test substance from the substrate. The membrane utilized is preferably a metallic disk. For example, a disk of aluminum that is 0.080 inches in thickness serves as a suitable membrane when the test substance employed is an adhesive or a coating, such as paint. When the test substance is a coating material bonded to the substrate, an overcoat adhesive layer is interposed between the first side of the membrane facing the test substance and the test substance employed. The overcoat adhesive layer bonds the membrane to the test substance with a bond having an adhesive strength greater than the strength of the bond between the test substance and the substrate.

It is quite important for the substrate to be of rigid construction. Otherwise the accuracy of the test will be affected if the substrate deforms. In preparing samples of test substances it is often convenient to apply the test substance to a relatively thin sheet of stainless steel, aluminum, or wood. To ensure that the substrate remains rigid during testing, it is sometimes advisable to provide the system with a rigid substrate reinforcement firmly secured to the substrate on a side thereof opposite the test substance. The substrate reinforcement must have an aperture therethrough that is aligned with the aperture through the substrate. The substrate reinforcement provides enhanced rigidity to the substrate and thereby prevents any errors from occurring due to any deformation of the substrate.

In another broad aspect the invention may be considered to be a method for testing the bond strength of a test substance adhesively bonded to a substrate. The method is comprised of the steps of: forming an aperture through the substrate; covering the aperture with a thin film positioned atop the substrate and extending beyond the perimeter of the aperture; applying the test substance to the substrate and to the thin film so as to bond the test substance to the substrate while encapsulating the film between the test substance and the substrate; bonding the first surface of a membrane to the test substance, the adhesive strength of the bond between the membrane and the test substance being greater than the adhesive strength of the bond between the test substance and the substrate; and determining the critical pressure required to substantially debond from the substrate a continuous periphery of an area of the test substance covering the film and the substrate, the critical pressure being directly related to the specific work of debonding.

In the implementation of the method the step of determining the critical pressure is preferably comprised of: determining the strength of the bond between the test substance and the substrate as a function of the specific work of substantially debonding the test substance from the substrate. The step of determining the critical pressure is further preferably comprised of: measuring the pressure at the moment the bond between the test substance and the substrate fails.

As previously noted, the invention is applicable to both a determination of the strength of an adhesive bond between the test substance and the substrate, and also a determination of the strength of the internal cohesive bond created within the test substance itself. In testing the cohesive bond strength within the test substance, the step of determining the critical pressure further comprises the step of determining the internal cohesive strength within the test substance as a function of the specific work of creating substantial cohesive failure within the test substance. In this application the step of determining the critical pressure is further comprised of measuring the pressure at the moment that substantial cohesive failure occurs within the test substance.

Preferably the method of the invention is performed by providing a membrane that remains approximately elastic when subjected to the pressure applied to debond the test substance from the substrate. When the method is performed with respect to a coating, as opposed to an adhesive, it is necessary to bond the membrane to the test substance utilizing an overcoating adhesive.

It is important for the thin film to remain in position covering the aperture in the substrate. While, with great care, this can be achieved simply by placing the thin film atop the substrate centered above the fluid aperture therethrough such that the periphery of the thin film rests upon the surface of the substrate surrounding the aperture, preferably the thin film is provided with a film adhesive prior to covering the aperture with the thin film. The film adhesive bonds the film to the substrate with a bond strength less than the strength of the bond between the test substance and the substrate. Also, to guard against inaccuracies caused by any deformation of the substrate, it is sometimes advisable to reinforce the substrate with a reinforcement backing having a backing aperture therethrough aligned with the aperture through the substrate prior to determining the critical pressure.

The invention may be described with greater clarity and particularity by reference to the accompanying drawings.

DESCRIPTION OF THE EMBODIMENTS AND IMPLEMENTATION OF THE METHOD

FIGS. 1–5 illustrate a system for testing the strength of a bond between a test substance 12 and a rigid substrate 14 through which an aperture 16 is defined. The substrate 14 may, for example, be formed of a disk of 6061 aluminum, three inches in diameter and one-quarter of an inch in thickness. Alternatively, the substrate 14 could be formed of stainless steel or any other metal, as well as other materials, such as wood, plastic, or plaster. The choice of the substrate 14 is determined by the substrate of interest to which the test material 12 is likely to be applied on a commercial basis. For example, if it is desired to test the strength of an adhesive bond that a particular adhesive substance 12 exhibits with respect to aluminum, an aluminum disk 14 of the type described forms an appropriate substrate 14.

Figure 1:
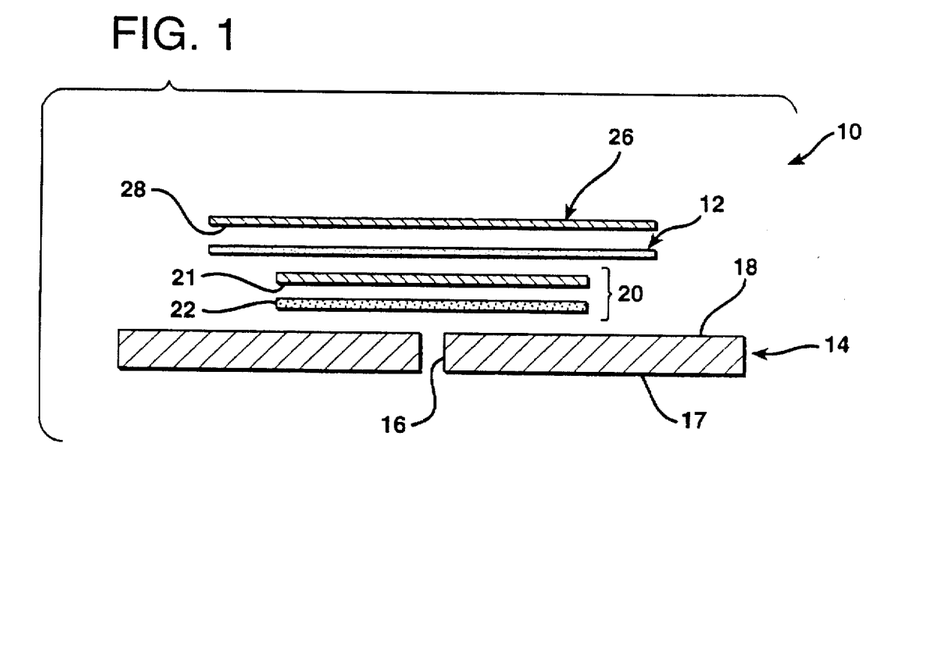
FIG. 1 is an exploded elevational view illustrating the component layers of substances and materials employed in a test assembly for testing the bonding strength of an adhesive according to the invention.

Prior to testing the substrate 14 is first prepared for bonding. Aluminum substrates 14 are typically prepared for bonding by dipping in a diluted solution of phosphoric acid for about a minute. A stainless steel substrate 14, on the other hand, would typically be dipped in a hot solution of diluted sulfuric acid as set forth in ASTM Standard D-2651, procedure 8, which is a standard recommended practice for preparation of metal surfaces for adhesive bonding.

A hole 16 may be drilled in the substrate 14 either before or after the surface preparation of the substrate 14. For an aluminum substrate 14 having the specifications previously set forth, an aperture 16 having a diameter of one-eighth of an inch is appropriate to allow the passage of fluid under pressure. If the aperture 16 is drilled after surface preparation, considerable care must be taken to ensure that no oil, grease, or other foreign matter is introduced onto the upper surface 18 of the substrate 14 to which the adhesive 12 is to be applied.

Once the substrate 14 has been fabricated and prepared for testing, it is covered with a thin film disk 20. The film disk 20 is provided for covering the aperture 16 and is interposed between the test substance 12, which in the example depicted is an adhesive to be tested, and the substrate 14.

The thin film 20 may be produced from a composite structure formed by a polyester backing 21, the underside of which has been coated with a weak film adhesive layer indicated at 22, which may be an acrylic adhesive. The thin film disks 20 may be formed as circles die cut from a pressure-sensitive tape and mounted on a strip coated with a release agent prior to use. Each disk 20 is cut to have a diameter of one and one-half inches. Suitable tapes from which the thin film disks 20 may be fabricated are sold commercially by 3M Company, located in Minneapolis, Minn., as 3M Protective Tapes. One suitable tape is sold as Part No. 1614.

A thin film disk 20 with the weak adhesive coating 22 on the underside of the backing 21 is positioned on the surface 18 of the substrate 14, centered atop the aperture 16. The periphery of the thin film disk 20 extends beyond the perimeter of the aperture 16 and contacts the upper surface 18 of the substrate 14. The composite thickness of the tape formed by the polyester backing 21 and the acrylic adhesive layer 22 on the underside thereof is about 0.0013 inches. Once the thin film disk 20 is centered atop the aperture 16, the film adhesive 22 is pressed into contact with the surface 18 of the substrate 14. The layer 12 of test substance is then applied across the entire substrate 14, covering both the upper surface of the thin film 20 and the peripheral area of the surface 18 of the substrate 14 surrounding the film 20.

A membrane 26 is provided and is preferably made of a relative strong material which remains substantially or at least approximately elastic during the test. That is, the membrane 26 can withstand the conditions of the test without greatly exceeding its elastic limit. For example, a thin layer of steel, metal foil, or a strong composite material may be utilized as the membrane 26. The membrane 26 may, for example, be formed of a disk of 7075-T6 aluminum that is two and one-quarter inches in diameter and 0.010 inches in thickness. The membrane 26 is first subjected to the same surface preparation as the substrate 14. The membrane 26 is then positioned with a first side 28 thereof facing the adhesive 12 to be tested. The membrane 26 is then pressed downwardly into contact with the adhesive 12. The adhesive 12 is then cured according to the specifications of the adhesive manufacturer.

Figure 2:
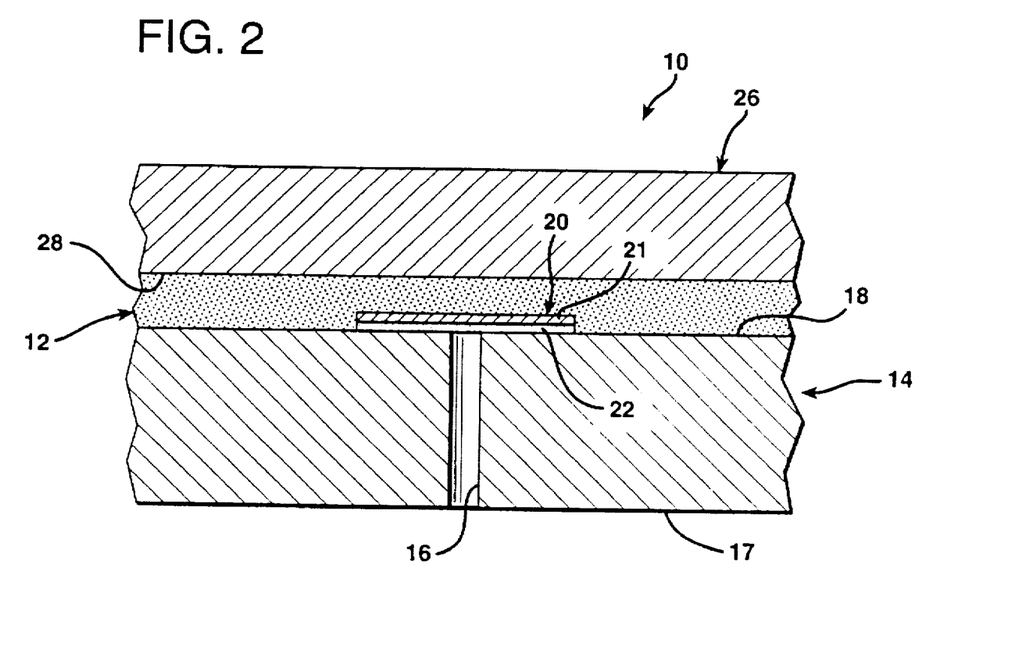
FIG. 2 is a sectional elevational detail showing the layers of component elements of FIG. 1 prior to testing as employed in the testing system according to the invention.

Curing of the adhesive 12 produces the test assembly 10, as shown in FIG. 2, which is a composite structure formed of the layers including the substrate 14, pressure-sensitive acrylic adhesive 22, polyester backing 21, test adhesive 12, and membrane 26. The test assembly 10 is then placed in the test fixture 30 illustrated in FIGS. 3 and 4. The test fixture 30, with the test assembly 10 depicted in FIGS. 1 and 2 encased therein, is then used to test the strength of the bond established between the test adhesive 12 and the substrate 14.

Figure 3:
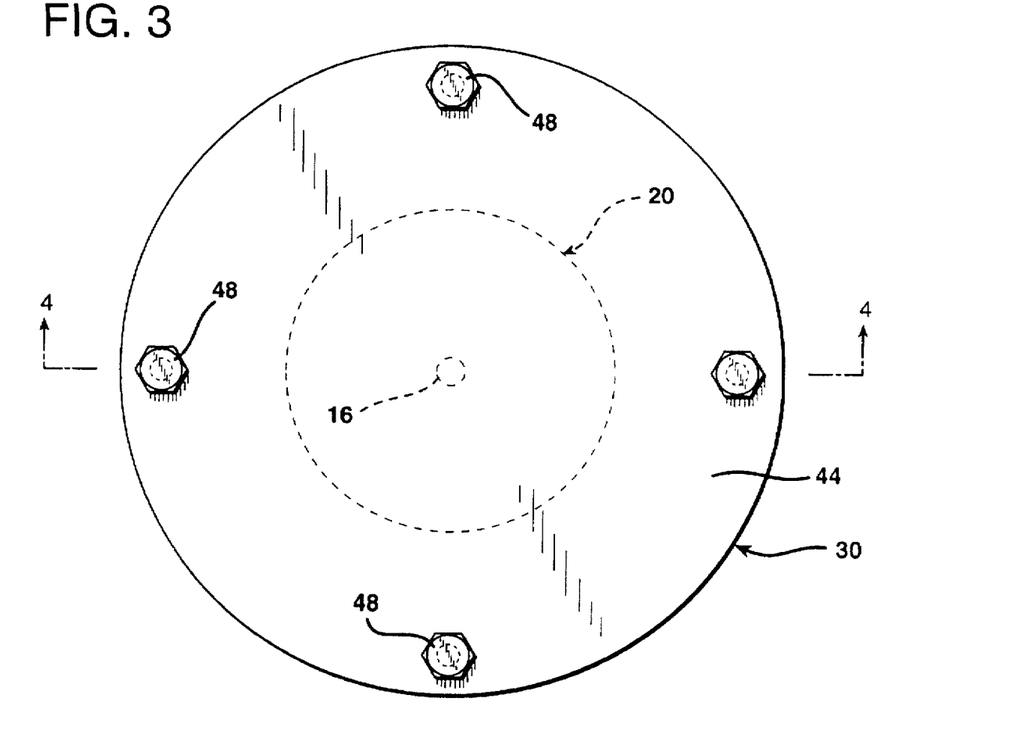
FIG. 3 is a top plan view of a test fixture employed in the test system of the invention.
Figure 4:
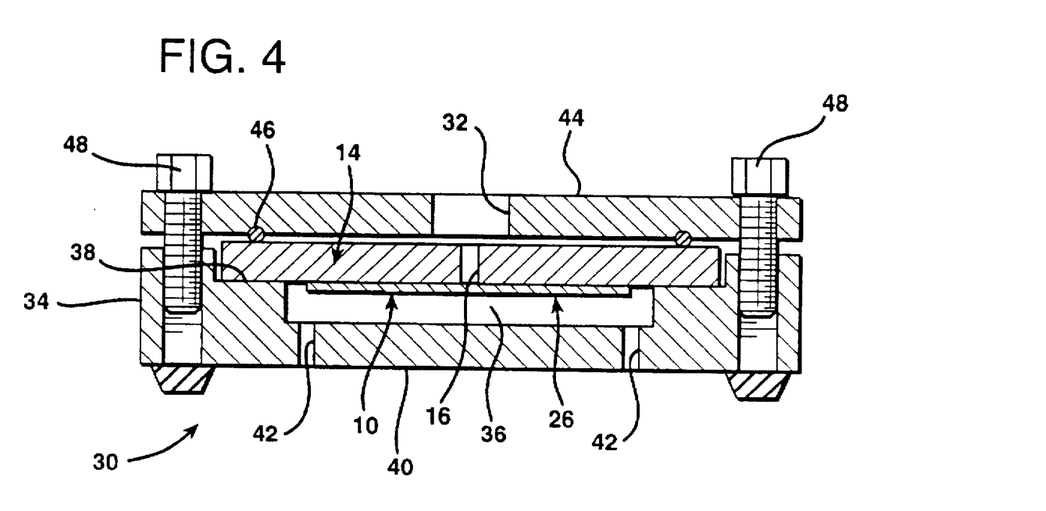
FIG. 4 is a sectional elevational view taken along the line 4—4 of FIG. 3.

The test fixture 30 is illustrated in detail in FIGS. 3 and 4 and is fabricated as a generally disk-shaped or cylindrical-shaped structure. The test fixture 30 employs a steel base 34 shaped generally in the form of a disk-shaped tray. The base 34 is provided with a central cavity 36 therewithin bounded about its outer periphery by an upright annular outer wall forming an annular seating ledge 38, and at its bottom by a floor 40. The floor 40 is provided with a plurality of fluid outlets 42 therethrough.

The test fixture 30 also includes a disk-shaped steel cover 44 in the center of which the central, axial fluid inlet port 32 in defined. The underside of the cover 44 is provided with an annular groove therein adapted to receive the O-ring 46.

The outer wall of the base 34 has four, internally-tapped bores located near its outer periphery and spaced at 90-degree intervals to receive externally threaded cap screws 48. The cover 44 has four peripheral openings therethrough that are aligned with the internally-tapped bores in the wall of the base 34. With the cover 44 removed, the test assembly 10 of FIGS. 1 and 2 is inverted and placed into the cavity 36, with the surface 18 of the substrate 14 resting atop the peripheral ledge 38 defined in the base 34.

With the O-ring 46 in position in the groove of the cover 44, the cover 44 is secured to the base 34 by engaging and tightening all four cap screws 48. The threaded shanks of the cap screws 48 are passed through the four openings defined near the periphery of the cover 44 that are aligned with the tapped bores in the fixture base 34. The threaded shanks of the cap screws 48 are engaged in the tapped bores in the walls of the fixture 34 and tightened to compress the cover 44 toward the bearing ledge 38 of the fixture base 34. Continued tightening of the cap screws 48 causes the substrate 14 to compress the O-ring 46 thereby creating a fluid-tight seal between the surface 17 of the substrate 14 and the cover 44 of the fixture 30. The test assembly 10 is thereupon tightly clamped within the test fixture 30.

Figure 5:
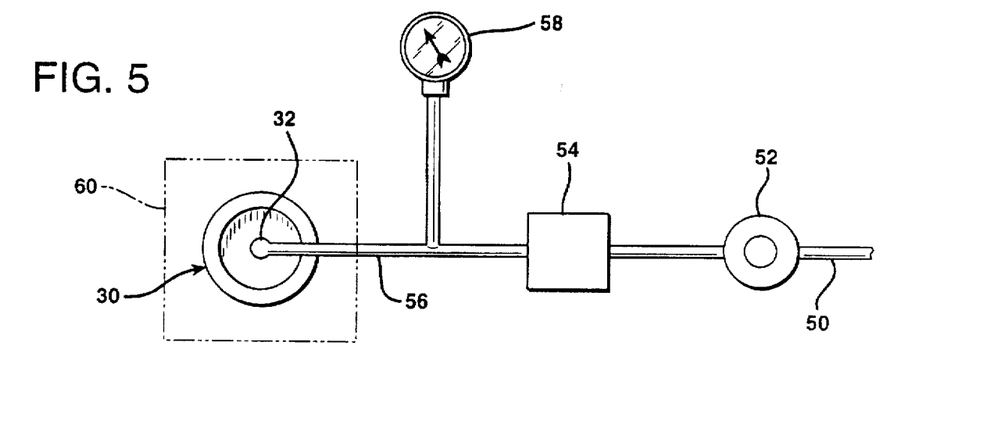
FIG. 5 is a diagrammatic view of a system constructed according to the invention.

The test fixture 30 is then connected to a fluid pressure source, not shown, in the manner depicted in FIG. 5. FIG. 5 illustrates diagrammatically a typical testing system according to the invention in which an inert gas or liquid is applied under pressure to the test fixture 30. The external source of pressurized fluid, such as nitrogen, is provided to line 50. The pressure of the fluid is adjustable by a pressure regulator 52. A valve 54 controls the flow of the fluid to the test fixture 30 through a coupling line 56. The coupling line 56 is coupled to the fluid aperture 16 in the substrate 14 through the pressure inlet port 32. A pressure gauge 58 measures the pressure of the fluid within the test system. The pressure gauge 58 may be a mechanical or digital device, and has the capability of recording maximum pressure measurements and indicates the scale pressure of the highest pressure that is registered within the test fixture 30.

In the operation of the system of the invention the composite structure 10 is enclosed within the test fixture 30 as previously described. Pressurized fluid is supplied to the test fixture 30 and pressure is increased until the test substance, namely the adhesive layer 12, debonds from the substrate 14. The pressure at the moment of debonding is recorded as the critical pressure.

The following formula is used to determine the bonding strength: $G=m\ P^n$, where "G" is the specific work of the debonding, "P" is the critical pressure, and "m" and "n" are constants inherent to the system design. After the system check is completed, it is necessary only to observe the critical pressure. Critical pressure may be taken directly from the pressure gauge 58, and the specific work of debonding may be determined in any system of units, (e.g., English, metric, or SI), using a digital system.

The test fixture 30 may be placed in a chamber 60 during testing to determine the effects of environmental conditions, such as extreme temperatures or corrosive atmospheres, upon the adhesive strength of a material. To further evaluate the effects of a corrosive environment upon adhesive strength, a corrosive gas or liquid may be used as the pressurizing fluid.

The strength of the bond of the pressure-sensitive adhesive layer 22 is quite weak as compared with both the bond formed by the test adhesive 12 with the upper surface 18 of the substrate 14 and also the bond formed between the membrane 26 and the test adhesive 12. In addition, the adhesive strength of the bond between the membrane 26 and the test adhesive 12 is greater than the strength of the bond between the test adhesive 12 and the substrate 14.

Figure 6:
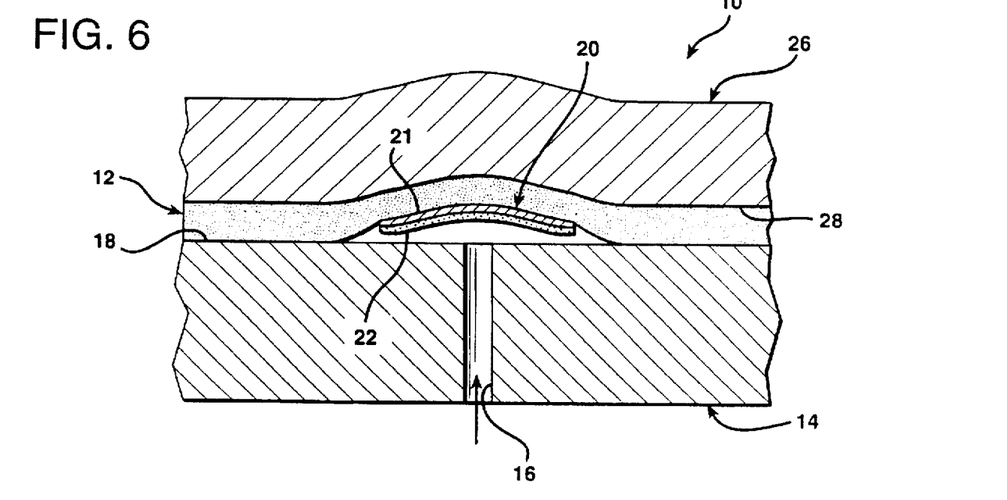
FIG. 6 is a sectional elevational detail illustrating failure of an adhesive bond in determining the adhesive strength of a test substance according to the invention.

The failure of the bond of the test substance may occur as either an adhesive failure or as a cohesive failure. FIG. 6 illustrates the failure of the adhesive bond between the test adhesive 12 and the substrate 14 when the failure occurs as a separation of the adhesive layer 12 from the substrate 14. Pressure applied through the pressure inlet port 32 leading to the fluid aperture 16 in the substrate 14 readily debonds the pressure-sensitive adhesive layer 22 from the surface 18 of the substrate 14. However, in an adhesive failure the pressure-sensitive adhesive 22 and thin film disk 20 thereatop will remain flat against the surface 18 of the substrate 14 until adhesive failure of the bond of the test adhesive 12 with the substrate 14 occurs.

The test assembly 10 is depicted at the moment of failure in FIG. 6, during which the area of the adhesive layer 12 just beyond the perimeter of the thin film 20 begins to separate from the surface 18 of the substrate 14. Once separation commences, it progresses rapidly radially outwardly until the membrane 26, with the test adhesive 12 still adhesive-bonded thereto pops entirely free of the substrate 14. The membrane 26 is constrained in its movement by the floor 40 of the cavity 36, however.

Figure 7:
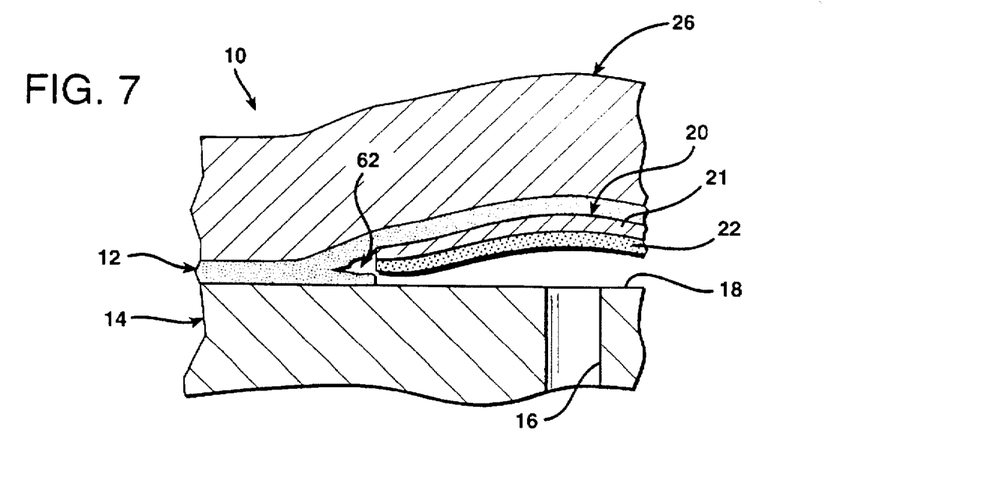
FIG. 7 is a sectional elevational detail illustrating cohesive failure in determining the internal cohesive bonding strength of a test substance according to the invention.

Alternatively, the system may be utilized to test cohesive failure as well. FIG. 7 illustrates the system of the invention at the moment of cohesive failure within the test adhesive 12. As in the failure of the adhesive bond of the test adhesive 12, the pressure-sensitive adhesive bond of the pressure-sensitive adhesive layer 22 with the surface 18 of the substrate 14 fails almost at once.

As depicted in FIG. 7, this failure occurs due to internal separation within the test adhesive 12, indicated generally at 62. That is, a portion of the adhesive 12 remains adhesively secured to the surface 18 of the substrate 14, but the portion immediately adjacent thereto gives way and a fracture forms within the structure of the test adhesive 12, as depicted. When cohesive failure occurs as depicted in FIG. 7, the critical pressure registered by the pressure gauge 58 is the pressure required to cause substantial cohesive failure within the test adhesive 12. In this application the gauge 58 measures the pressure at the moment substantial internal cohesive failure within the test adhesive 12 occurs. In either mode of failure the membrane 26 remains elastic when subjected to the pressure applied to debond the test adhesive 12 from the substrate 14 or to cause cohesive failure.

Figure 8:
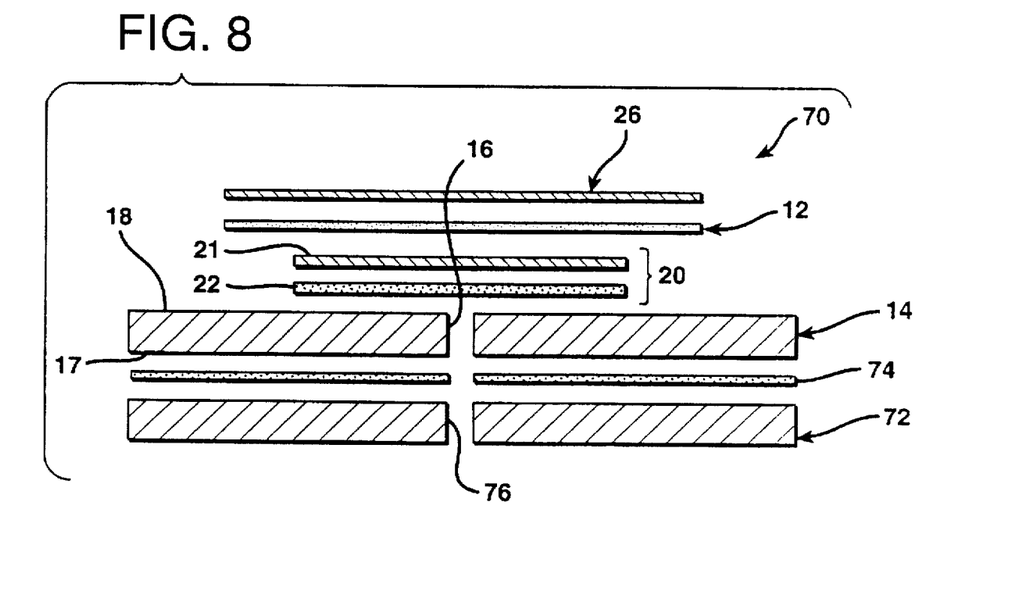
FIG. 8 is an exploded elevational view illustrating the layers and component elements of a test assembly for testing an adhesive alternative to that depicted in FIG. 1.

In some situations it may prove necessary to reinforce the substrate 14 to ensure that it remains rigid and does not deform before the critical pressure is reached. FIG. 8 illustrates another test assembly 70, utilized in the test fixture 30 in the manner previously described, which includes the same component substances and layers as the test assembly 10. In addition the test assembly 70 also includes a "doubler" which is formed of another aluminum disk 72 having a size and construction identical to the substrate 14. The reinforcement disk 72 is secured to the substrate 14 by means of a layer 74 of very high-strength adhesive. The adhesive layer 74 may, for example, be an adhesive manufactured by Hysol Manufacturing, located in Richmond, Calif., manufacturers adhesive No. 9330 with 0.003 inch diameter glass beads therein.

The reinforcement disk 72 also has a one-eighth inch diameter aperture 76 drilled through its center. In securing the reinforcement backing 72 to the substrate 14 utilizing the adhesive 74, care is taken to ensure that the apertures 76 and 16 are in substantial coaxial alignment. The test assembly 70 is clamped within the test fixture 30 and pressure is applied until the critical pressure is reached in the manner previously described.

Figure 9:
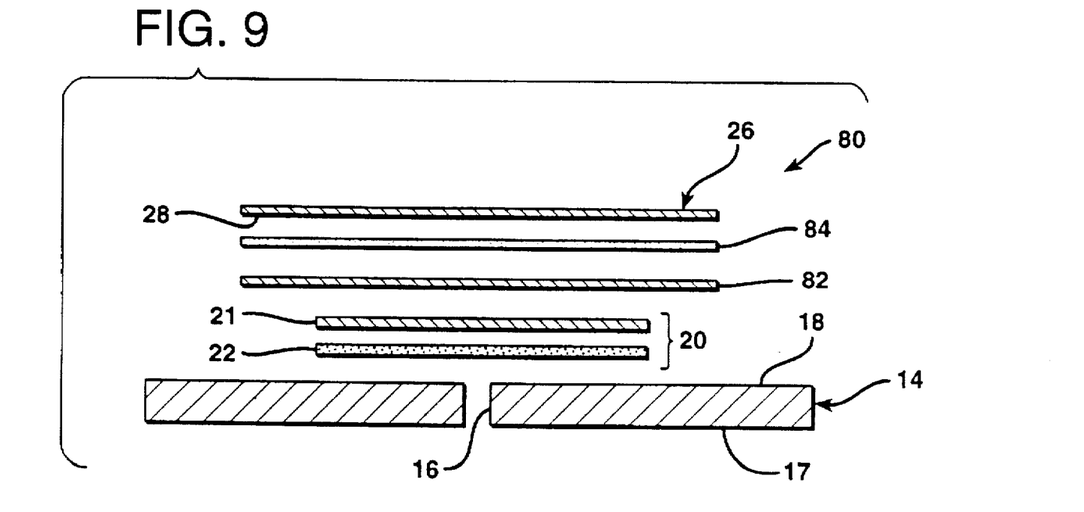
FIG. 9 is an exploded elevational view illustrating the layers and component elements in a test assembly for testing the bonding strength of a coating according to the invention.
Figure 10:
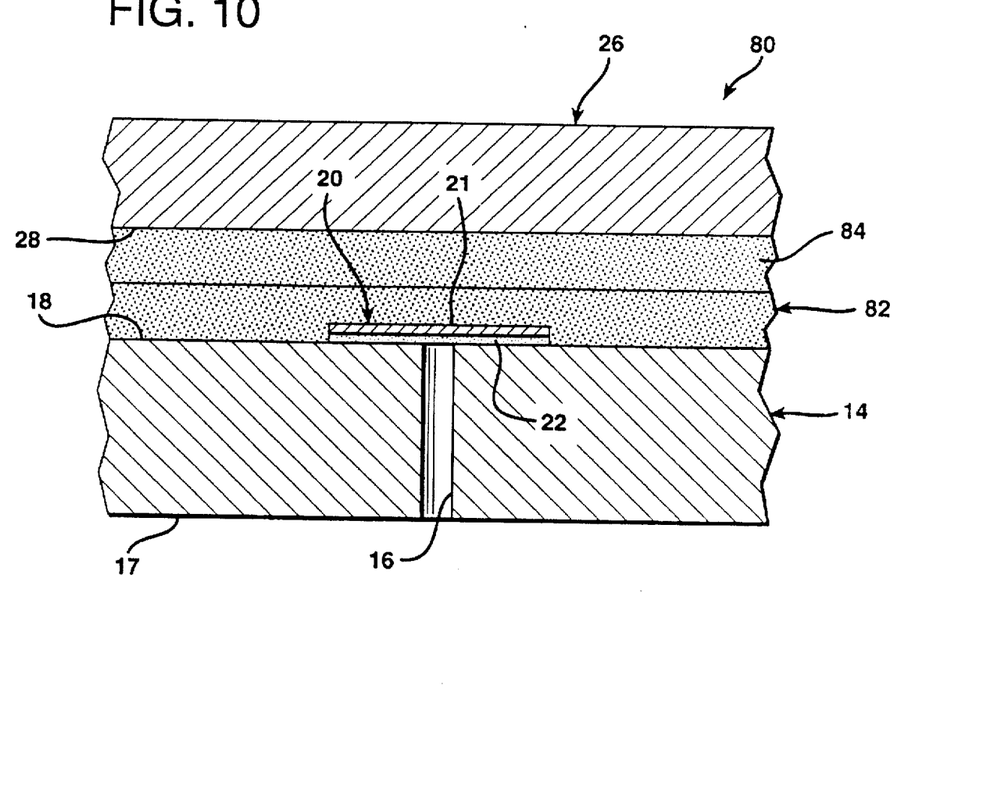
FIG. 10 is a sectional elevational detail illustrating the layers of component elements of FIG. 9 prior to testing.

FIGS. 9 and 10 illustrate a further test assembly 80 employed in conjunction with the test fixture 30 in the system of the invention. The substrate 14 and the thin film disk 20 are identical to those depicted and described in FIGS. 1–4. The test substance, however, is a coating layer 82 which is typically not an adhesive. The coating 82 is more typically paint, varnish, or some other substance applied in liquid form and cured to form a shell-like coating. Nevertheless, by its nature the coating 82 exerts a substantial adhesive bond with the surface 18 of the substrate 14. Alternatively, an adhesive tape may be substituted for the coating 82 and its bonding strength tested.

The substrate 14 is prepared in the manner previously described in conjunction with the embodiment of FIGS. 1–4, and the thin film disk 20 is positioned atop the surface 18 of the substrate 14 with the pressure-sensitive adhesive 22 weakly adhering to the surface 18, as described in conjunction with drawing FIGS. 1–4. Thereafter, a layer of paint is applied in liquid form across the periphery of the surface 18 of the substrate 14 and across the exposed surface of the thin film disk 20. This layer of paint is then allowed to cure to form the coating 82.

After the coating 82 has dried, an overcoat adhesive layer 84 is applied in liquid form atop the coating 82. The adhesive layer 84 may be the same high-strength cement No. 9330 produced by Hysol Manufacturing previously described. Once the overcoat adhesive layer 84 has been applied atop the coating 82, the aluminum membrane 26, constructed and prepared as previously described, is placed atop the adhesive layer 84. The test assembly 80 is then compressed as depicted in FIG. 10. The overcoat adhesive layer 84 between the first side 28 of the membrane 26 bonds the membrane 26 to the coating 82 to be tested such that the adhesive strength of the bond between the membrane 26 and the adhesive coating 82 being tested is greater than the strength of the bond between the coating 82 and the substrate 14.

The test assembly 80 is then positioned in the test fixture 34 in place of the test assembly 10 in the manner depicted and described in conjunction with FIG. 4. Pressure is then applied through the pressure inlet port 32 and the critical pressure is determined in the manner previously described in conjunction with drawing FIGS. 1–7.

Figure 11:
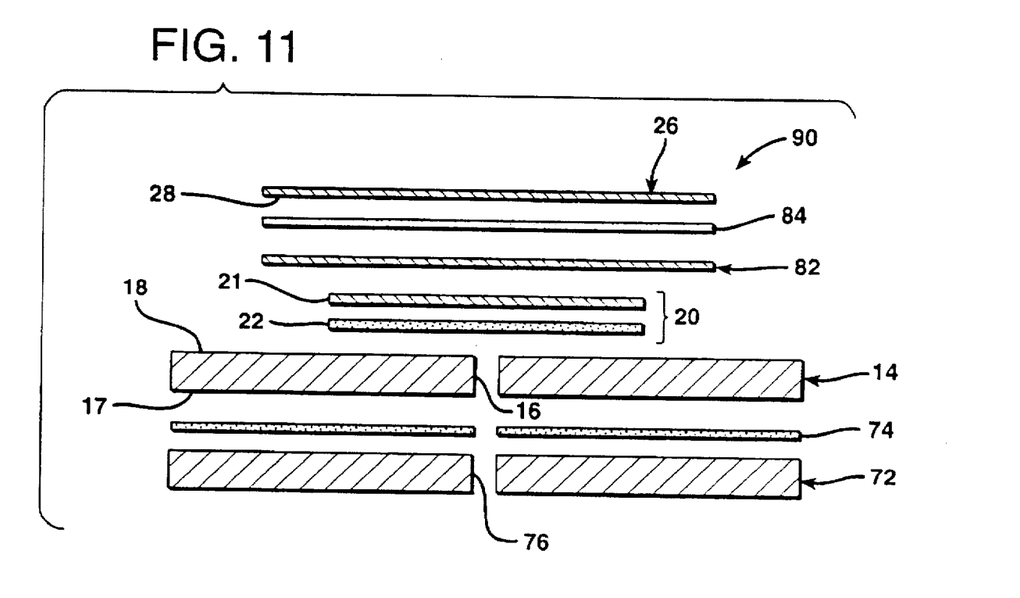
FIG. 11 is an exploded elevational view of a test assembly for testing the bonding strength of a coating alternative to that depicted in FIG. 9.

In some circumstances it may be necessary to provide a test assembly such as that depicted in FIGS. 9 and 10 with further reinforcement, comparable to that depicted and described in conjunction with FIG. 8. FIG. 11 illustrates a test assembly 90 that includes all of the layers, components, and substances of the test assembly 80 shown in FIG. 9. In addition, the test assembly 90 further includes a "doubler" which is formed of the same rigid substrate reinforcement backing 72 employed as depicted and described in conjunction with FIG. 8 utilizing the layer 74 of Hysol adhesive employed in the embodiment of FIG. 8. The rigid substrate reinforcement backing 72 is firmly secured to the substrate 14 on the side 17 thereof opposite the test substance, which is the coating 82. As in the embodiment of FIG. 8, the substrate reinforcement backing 72 employed in the test assembly 90 has an aperture 76 therethrough aligned with the aperture 16 through the substrate 14.

Undoubtedly, numerous variations and modifications of the invention will become readily apparent to those familiar with adhesion testing systems. For example, any number of different materials may be employed to form the substrate, the thin film for covering the aperture in the substrate, the test substance, the membrane, and the adhesive bonding the test substance to the membrane (if any). Accordingly, the scope of the invention should not be construed as limited to this specific embodiments of the invention depicted nor the specific implementations of the method described.

I claim:

1. A system for testing the strength of a bond between a test substance and a rigid substrate through which an aperture is defined comprising:

a membrane with a first side bonded to the test substance, the adhesive strength of the bond between the membrane and the test substance being greater than the strength of the bond between the test substance and the substrate;

a thin film for covering the aperture interposed between the test substance and the substrate atop the aperture and extending beyond the perimeter of the aperture;

means for applying increasing pressure through the aperture in the substrate to debond the test substance from the substrate; and means for determining the critical pressure required to substantially debond a continuous periphery of an area in the test substance from the substrate, the critical pressure being directly related to the specific work of debonding.

2. The system of claim 1 wherein the means for determining the critical pressure further comprises;

means for determining the adhesive strength of the bond between the test substance and the substrate directly from the pressure required to cause substantial bond failure as a function of the specific work of debonding the test substance from the substrate; and wherein the means for determining the critical pressure further comprises:

means for measuring the pressure at the moment the bond between the test substance and the substrate fails.

3. The system of claim 1 in which the membrane remains elastic when subjected to the pressure applied to debond the test substance from the substrate.

4. The system of claim 1 wherein the test substance is an adhesive material bonded to the substrate.

5. The system of claim 1 wherein the test substance is a coating material bonded to the substrate and further comprising an overcoat adhesive layer between the first side of the membrane and the test substance, wherein the overcoat adhesive layer bonds the membrane to the test substance as aforesaid.

6. The system of claim 1 wherein the coating material is comprised of paint.

7. The system of claim 1 further comprising a rigid substrate reinforcement firmly secured to the substrate on a side thereof opposite the test substance, and wherein the substrate reinforcement has an aperture therethrough aligned with the aperture through the substrate.

8. A system for testing the cohesive strength of a test substance bonded to a rigid substrate through which an aperture is defined comprising:

a membrane with a first side bonded to the test substance, the adhesive strength of the bond between the membrane and the test substance being greater than the cohesive strength of the test substance;

a thin film for covering the aperture interposed between the test substance and the substrate atop the aperture and extending beyond the perimeter of the aperture;

means for applying increasing pressure through the aperture in the substrate to cause cohesive failure in the test substance; and means for determining the critical pressure required to cause cohesive failure around a continuous periphery of an area in the test substance, the critical pressure being directly related to the specific work of cohesive failure.

9. The system of claim 8 wherein the means for determining the critical pressure further comprises:

means for determining the internal cohesive strength of the test substance directly from the pressure required to cause substantial cohesive failure therewithin, and wherein the means for determining critical pressure further comprises:

means for measuring the pressure at the moment substantial cohesive failure within the test substance occurs.

10. The system of claim 8 in which the membrane remains elastic when subjected to the pressure applied to debond the test substance from the substrate.

11. The system of claim 8 wherein the test substance is an adhesive material bonded to the substrate.

12. The system of claim 8 wherein the test substance is a coating material bonded to the substrate and further comprising an overcoat adhesive layer between the first side of the membrane and the test substance, wherein the overcoat adhesive layer bonds the membrane to the test substance as aforesaid.

13. The system of claim 8 wherein the coating material is comprised of paint.

14. The system of claim 8 further comprising a rigid substrate reinforcement firmly secured to the substrate on a side thereof opposite the test substance, and wherein the substrate reinforcement has an aperture therethrough aligned with the aperture through the substrate.

15. A method for testing the strength of a test substance bonded to a substrate comprising the steps of:
- forming an aperture through the substrate;
- covering the aperture with a thin film positioned atop the substrate and extending beyond the perimeter of the aperture;
- applying the test substance to the substrate and to the thin film so as to bond the test substance to the substrate while encapsulating the film between the test substance and the substrate;
- bonding the first surface of a membrane to the test substance, the adhesive strength of the bond between the membrane and the test substance being greater than the adhesive strength of the bond between the test substance and the substrate; and
- determining the critical pressure required to create a failure of the test substance around a continuous periphery of an area of the test substance covering the film and the substrate.

16. The method of claim 15 wherein the step of determining the critical pressure further comprises:
- determining the strength of the bond between the test substance and the substrate as a function of the specific work of substantially debonding the test substance from the substrate, by measuring the pressure at the moment the bond between the test substance and the substrate fails.

17. The method of claim 15 wherein the step of determining the critical pressure further comprises the step of:
- determining the internal cohesive strength within the test substance as a function of the specific work of creating substantial cohesive failure within the test substance by measuring the pressure at the moment that substantial cohesive failure occurs within the test substance.

18. The method of claim 15 further comprising the step of:
- bonding the membrane to the test substance utilizing an overcoating adhesive.

19. The method of claim 15 further comprising holding the thin film in position covering the aperture by first coating the underside of the thin film with a film adhesive that bonds the film to the substrate with a bond strength less than the strength of the bond between the test substance and the substrate prior to covering the aperture with the thin time.

20. The method of claim 15 comprising the further step of reinforcing the substrate with a reinforcement backing having a backing aperture therethrough aligned with the aperture through the substrate prior to determining the critical pressure.

* * * * *